(12) United States Patent
Vervoort (10) Patent No.: US 9,004,065 B2
(45) Date of Patent: Apr. 14, 2015

(54) DEVICE FOR PROVIDING A BREATHING GAS

(75) Inventor: Marinus Jacobus Vervoort, Monnickendam (NL)

(73) Assignee: Institute "On My-Way" B.V., Monnickendam (NL)

( * ) Notice: Subject to any disclaimer, the term of this patent is extended or adjusted under 35 U.S.C. 154(b) by 936 days.

(21) Appl. No.: 12/673,711

(22) PCT Filed: Apr. 24, 2008

(86) PCT No.: PCT/NL2008/000111
§ 371 (c)(1),
(2), (4) Date: Sep. 16, 2010

(87) PCT Pub. No.: WO2009/022902
PCT Pub. Date: Feb. 19, 2009

(65) Prior Publication Data
US 2011/0005522 A1    Jan. 13, 2011

Related U.S. Application Data

(60) Provisional application No. 60/955,774, filed on Aug. 14, 2007.

(51) Int. Cl.
*A61M 16/00* (2006.01)
*F16K 31/02* (2006.01)
*A61M 16/16* (2006.01)
*A61F 7/00* (2006.01)

(52) U.S. Cl.
CPC ........ *A61M 16/16* (2013.01); *A61F 2007/0061* (2013.01); *A61M 2205/3606* (2013.01); *A61M 2205/3646* (2013.01)

(58) Field of Classification Search
USPC ............................ 128/204.15–204.16, 204.18
See application file for complete search history.

(56) References Cited

U.S. PATENT DOCUMENTS

| | | | |
|---|---|---|---|
| 4,010,748 A | | 3/1977 | Dobritz |
| 4,301,792 A | * | 11/1981 | Pasternack ............... 128/202.26 |
| 4,545,379 A | | 10/1985 | Jenkins |
| 4,829,997 A | | 5/1989 | Douwens et al. |
| 5,386,823 A | * | 2/1995 | Chen ......................... 128/204.15 |
| 5,542,413 A | * | 8/1996 | Horn ......................... 128/204.15 |

(Continued)

FOREIGN PATENT DOCUMENTS

| | | |
|---|---|---|
| WO | 2004060459 A1 | 7/2004 |
| WO | 2005070035 A2 | 8/2005 |
| WO | 2005113046 A2 | 12/2005 |

*Primary Examiner* — Rachel Young
(74) *Attorney, Agent, or Firm* — Browdy and Neimark, PLLC (57) ABSTRACT

A device for providing a breathing gas, in particular to a device for conditioning a breathing gas for stimulating weight reduction of a breathing creature. The device includes a gas supply mechanism and gas conditioning mechanism. The device provides a breathing creature with a breathing gas which is conditioned by adding particles including a frozen fluid to the breathing gas. When the breathing creature inhales the breathing gas, his body comes into contact with the gas and the particles including the frozen fluid. The breathing gas and the particles will be warmed by the body of the creature, preferably to a temperature at which the frozen fluid starts to melt. The warming of the particles and the breathing gas by the body of the breathing creature requires energy, and therefore stimulates the metabolism of a breathing creature, promoting fat burning and inducing weight reduction.

14 Claims, 2 Drawing Sheets

(56) References Cited

U.S. PATENT DOCUMENTS

| | | |
|---|---|---|
| 5,662,161 A | 9/1997 | Hughes et al. |
| 5,761,909 A | 6/1998 | Hughes et al. |
| 5,890,490 A * | 4/1999 | Aylsworth et al. ....... 128/203.12 |
| 6,547,811 B1 | 4/2003 | Becker et al. |
| 6,983,749 B2 * | 1/2006 | Kumar et al. ............ 128/204.15 |
| 8,100,123 B2 * | 1/2012 | Belson .................... 128/204.15 |
| 2003/0136402 A1 * | 7/2003 | Jiang et al. ............... 128/200.24 |
| 2004/0173214 A1 * | 9/2004 | Tinker ..................... 128/205.13 |
| 2005/0039757 A1 * | 2/2005 | Wood ....................... 128/207.18 |
| 2005/0229930 A1 * | 10/2005 | Donohue ................. 128/204.15 |
| 2006/0196510 A1 * | 9/2006 | McDonald et al. ...... 128/206.21 |
| 2006/0222720 A1 | 10/2006 | Yamashita |
| 2007/0023041 A1 * | 2/2007 | Wang ...................... 128/203.13 |
| 2007/0028921 A1 * | 2/2007 | Banner et al. ............ 128/204.21 |

* cited by examiner

DEVICE FOR PROVIDING A BREATHING GAS

FIELD AND BACKGROUND OF THE INVENTION

The invention relates to a device for providing a breathing gas, in particular to a device for conditioning a breathing gas, for managing the weight of a breathing creature, in particular for stimulating weight reduction. The invention further relates to a method and to a use of a device for conditioning a breathing gas and for providing said breathing gas to a breathing creature, for managing the weight of a breathing creature, in particular for stimulating weight reduction of the breathing creature.

In developed countries around the world, there is a tremendous interest in personal fitness, wellness and para medication. At the same time there is a disturbing trend that people, including adults and children are becoming overweight. By overweight, it is meant that the subject has exceeded the acceptable weight range and percent body fat generally considered as healthy determined by factors including, but not necessarily limited to age, height, sex, and body type.

Overweight produces a wide range of health concerns including sleep apnoea, orthopaedic complications, arterial sclerosis, diabetes, heart disease and also social and psychological problems etc. All these undesirable conditions contribute in development of an unsatisfactory quality of life and in some cases premature death.

Therefore, many people want to maintain a specific weight or even lose weight to maintain or enhance their physical condition. To lose weight the body needs to burn more energy than is provided by the food intake. Known diet methods include restriction of amounts and kinds of food, exercises and use of diet drugs to reduce or maintain body weight.

However, managing weight via known diet methods takes a long period of time, even when combined with exercises or diet drugs. Many people are not capable of maintaining a reduced food intake and/or an increased exercise level over a long period of time and therefore do not achieve the amount of weight loss aimed for or even gain weight in spite of there efforts. Also, even when the diet results in a loss of weight, for a variety of reasons, most people find it very difficult to maintain significant weight reduction over time.

Therefore only a few people are able to achieve a significant reduction of weight, and even less are able to maintain this condition.

SUMMARY OF THE INVENTION

It is an object of the invention to obviate the problems described hereinabove and in particular to enable weight reduction of a breathing creature.

The invention provides a device for providing a breathing gas, the device comprising gas supply means and gas conditioning means. Thus a device according to the invention can provide a breathing creature with a breathing gas. The breathing gas is conditioned by forming particles comprising a frozen fluid in the breathing gas. When the breathing creature inhales the breathing gas, his body comes into contact with the gas and the particles comprising the frozen fluid. The breathing gas and the particles will be warmed by the body of the creature, preferably to a temperature at which the frozen fluid melts.

The warming of the breathing gas and the particles by the body of the breathing creature requires energy. The energy used by the body in the process of warming up the breathing gas and particles is provided for by burning extra energy c.q. calories. Thus, a device according to the invention will increase the burning of energy by the body of the breathing creature and thus stimulate the metabolism of the breathing creature. This will help the breathing creature manage his weight, in particular to maintain a specific weight, or induce weight reduction of the breathing creature in a controlled manner.

Furthermore, by forming the particles in the breathing gas the capacity of the breathing gas to comprise energy is increased, because more energy is needed to warm or cool a breathing gas comprising such particles than for warming or cooling an unconditioned breathing gas. Thus, by conditioning the breathing gas, the potential of energy exchange between the body of the breathing creature and the breathing gas is increased. Therefore, the body of a breathing creature will, while breathing a breathing gas provided by a device according to the invention, use more energy than while breathing an unconditioned breathing gas of the same temperature.

The invention thus provides a device for conditioning a breathing gas to increase the energy consumption of a person inhaling the gas and thus increasing the metabolism of the person. A device according to the invention may therefore assist in managing the weight of a breathing creature, more in particular in managing the weight reduction of the breathing creature, and/or in maintaining the breathing creature at a specific weight.

It is noted that the particles may be formed in different ways. For example, a substance may be added in the form of a fluid, vapour or droplets, to a cooled breathing gas, the temperature of the breathing gas cooling the substance into a frozen fluid. Preferably, the fluid is added in the form of small droplets, which need less cooling than a gaseous fluid to obtain particles comprising frozen fluid. In a further preferred embodiment the droplets are cooled to a temperature slightly above to their freezing temperature prior to being added to the breathing gas. Alternatively, the particles can also be added to the breathing gas in frozen i.e. solid form, for example in the form of ice particles or ice crystals. Thus the gas can be conditioned in a limited amount of time.

The temperature of the conditioned breathing gas and/or the particles is lower than the body temperature of the breathing creature breathing the gas. In a preferred embodiment, the particles are frozen particles of a substance having a phase change, changing from solid to liquid and/or gas, below the body temperature of the breathing creature. Preferably the temperature of the conditioned breathing gas is such that the particles melt within the breathing ducts of the breathing creature, in particular in the back of the nose or throat such that remaining liquid can be swallowed by the user and does not run out of the nose of the creature. Thus, the frozen fluid is no longer part of the exhaled breathing gas and remains in the users' body where it is further warmed, retracting extra energy from the body.

A device according to the invention can be used for increasing the energy consumption of a passive breathing creature. For example a person may use the device while sleeping, watching television, driving a car, sunbathing at the beach or sitting behind a pc, thus stimulating his metabolism to reduce weight or to prevent weight gain.

Also, a device according to the invention may be used for increasing the metabolism of an active person. For example a breathing creature may use the device while running to further increase the energy consumption of his body. Furthermore, when used during exercising, the cooling effect of the breathing gas may prevent overheating of the body and allow the person to exercise for a prolonged period of time.

Also, by cooling the body of the user during exercising, less natural body fluid is lost via transpiration. In addition, fluid from molten particles may remain in the body of the user. Thus, the intake of fluid by the person during exercise is less critical and the risk of dehydration is reduced. Furthermore, after exercising the device may be used to reduce the temperature of the body to a normal level more quickly, thus enhancing the recuperation of the body.

Also, by nature the mucous membrane comprised in the breathing ducts, lungs and nasal cavity is humid. During intense exercise, especially when breathing dry air, a lot of the fluid of the mucous membrane is absorbed by the breathing gas, and thus removed from the body. A device according to the invention may reduce the loss of fluid from the mucous membrane, and thus prevent damage to the membrane, by adding fluid to the breathing gas. It can be used to provide a conditioned breathing gas to the user prior to, during, or after exercising.

Thus the invention provides a device for enhancing the physical condition, and hence the performance of a breathing creature such as a human being.

The invention furthermore relates to a method for managing the weight reduction of a breathing creature, for example a human, by supplying a breathing gas to the nose of the creature with the device according to the invention.

The invention also relates to the use of a device according to the invention for conditioning a breathing gas by lowering the temperature of the breathing gas to induce weight reduction and/or prevent weight gain of a person breathing the conditioned breathing gas.

Further objects, embodiments and elaborations of the device and the method according to the invention will be apparent from the following description, in which the invention is further illustrated and elucidated on the basis of a number of exemplary embodiments, with reference to the drawings.

DETAILED DESCRIPTION

Figure 1:
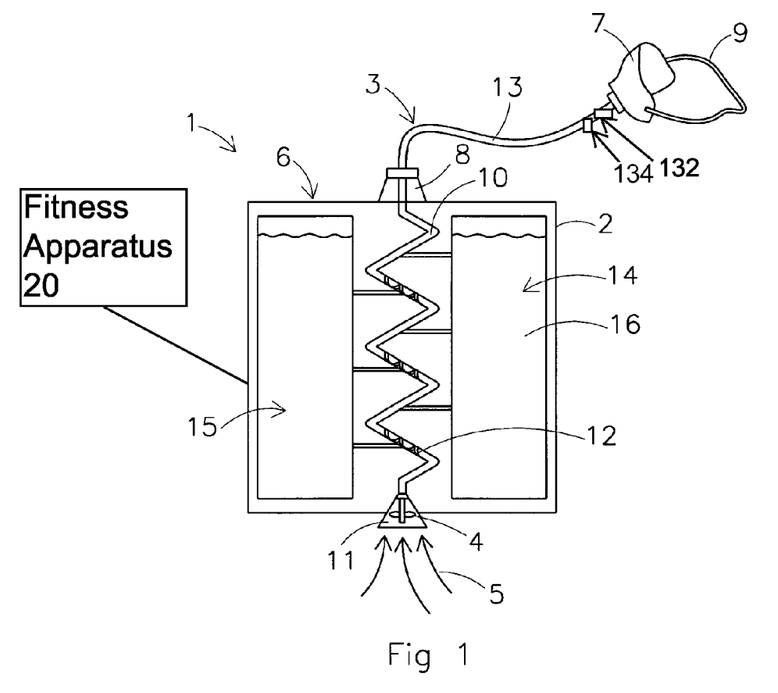
FIG. 1 is a schematic view in section of a device according to the invention.

First, the invention will be further elucidated on the basis of the schematic exemplary embodiment of a device according to the invention as shown in FIG. 1. Thereafter, some particular alternative embodiments will be described.

FIG. 1 shows a device 1 for providing a breathing gas according to the invention. The device 1 comprises gas conditioning means 6 for conditioning the breathing gas, and gas supply means 3 for supplying the breathing gas to the nose of a breathing creature, more specifically a human, using the device. The device is preferably of such size and weight that it can be worn on the body of the user without limiting his freedom of movement. The gas conditioning means 6 comprise a housing 2 provided with a gas inlet 11 and a gas outlet in the form of a connection valve 8 for connecting the gas supply means to the gas conditioning means. The gas conditioning means 6 further comprise a gas transport duct 10 for transporting a breathing gas from the gas inlet 11 to the valve 8. In the preferred embodiment shown, the gas conditioning means 6 are provided with a helical gas transport duct 10 which provides a long track for conditioning the gas while being compact in over all size.

As a drive means for transporting the breathing gas a fan 4 is provided near the air inlet 11. The fan is driven by a drive (not shown) to draw in air from the surroundings for use as a breathing gas. The pressure generated by the fan drives the air via the transport duct 10. The flow of the air drawn into the inlet 11 is indicated with arrows 5.

The gas conditioning means 6 are configured to form particles comprising a frozen fluid in the breathing gas. More in particular, the gas conditioning means are configured to cool the breathing gas and to condition the level of humidity of the breathing gas. For conditioning the breathing gas, the gas conditioning means 6 comprise cooling means 15 and humidifying means 14.

The cooling means 15, comprise a cooling duct 12, which spirals within the transport duct 10. The cooling means 15 further comprise means for transporting a cooling fluid via the cooling duct 12 for cooling a breathing gas transported via the transport duct 10.

The humidifying means 14 comprise a water reservoir 16 and means for humidifying the breathing gas by adding water from the reservoir in the form of small droplets to the breathing gas. Water from the reservoir may for example by injected under pressure via nozzles 17 into the gas transport duct, causing the water to form a mist of small droplets in the breathing gas. These droplets, due to their small size, are picked up and carried along by the flow of breathing gas. Alternatively, water may also be added to the breathing gas by an ultrasonic humidifier, which may be used to vaporize the water using an ultrasonic wave produced by means of a piezoelectric transducer.

The gas supply means 3 for supplying the breathing gas to a user's nose comprise a gas duct 13 and a gas outlet 7. The gas duct 13 is a hose made out of a flexible material such as plastic or rubber. At one end the gas duct 13 is provided with means for connecting the duct to the valve 8 of the gas conditioning means 6. At an opposite end, the gas duct 13 is provided with the gas outlet 7 which is configured to in use be located near an opening of the users' nose for providing a user with the conditioned breathing gas.

In the embodiment shown, the gas outlet 7 is provided in the form of a mask 9 comprising the actual gas outlet. The mask 9 is configured to in use be placed over the nose of a person, such that the actual outlet of the gas duct is positioned adjacent the opening of the user's nose. The mask 9, more in particular the actual gas outlet, is positioned near the opening of the nose by positioning means 9 in the form of an adjustable band. Alternatively, the gas supply means may for example be provided with a gas outlet and positioning means for positioning the outlet in the opening of the user's nose.

In addition, or as an alternative, to the drive means provided in the gas conditioning means 6, the gas supply means 3 may also be provided with drive means for transporting the breathing gas.

For providing a breathing gas with the device 1 according to the invention, air is drawn in via the inlet 11 into the gas duct 10 and is transported via this gas duct to the valve 8. While the breathing gas is transported via the duct 10 it is cooled by the cooling duct 12 to a temperature below the freezing point of water. Preferably, the gas conditioning means are configured to condition the breathing gas such that the temperature of the breathing gas is between −30 and −1° C. and preferably between −15 and −1° C. When the breathing gas is cooled sufficiently the small water droplets added to the breathing gas will freeze to form frozen particles. Due to their small size, the droplets freeze quickly. The breathing gas is thus conditioned by adding particles to the gas, which particles comprise a frozen fluid.

To facilitate the absorption of the droplets by the breathing gas, the droplets are preferably added to the breathing gas in little concentrations and in intermediate steps. Thus the breathing gas, while transported via the transport duct 10, is subsequently subjected to stages of cooling the flow of breathing gas, droplets and/or particles, and to stages of adding more droplets to the flow of breathing gas. The breathing gas is preferably also cooled during and after the adding of the droplets to prevent the temperature of the breathing gas to rise above the freezing point of the added fluid. In a preferred embodiment the water, or alternative fluid, is cooled before it is added to the breathing gas, preferably to just above its freezing point. Thus the droplets do not need extensive cooling by the breathing gas to freeze into frozen particles. By providing the fluid via anti-drip nozzles, fluid freezing to the nozzle outlets may be prevented.

The embodiment shown is provided with a gas supply means for inhaling the conditioned breathing gas via the nose. The breathing gas comprising the frozen particles is transported via the flexible duct 13 and the gas outlet 7 of the supply means 3 to the nose of the user of the device 1. When the user inhales, the breathing gas enters the body of the user via the nose ducts. The biological function of the nose is to warm air on inhalation and remove moisture on exhalation. Thus, a breathing gas inhaled and/or exhaled via the nose will be more warmed than a breathing gas inhaled and/or exhaled via the mouth. Thus, providing the breathing gas via the nose will draw more energy from the body from the breathing creature and is thus beneficial for managing the weight of the breathing creature according to the invention.

In a preferred embodiment, the particles are frozen particles of a substance, such as water, having a phase change, changing from solid to liquid and/or gas, below the body temperature of the breathing creature. Preferably the temperature of the conditioned breathing gas, and or the temperature and/or size of the particles is such that the particles melt within the breathing ducts of the breathing creature, in particular in the back of the nose or throat such that remaining liquid can be swallowed by the user and does not run out of the nose of the creature. Thus the frozen fluid is no longer part of the exhaled breathing gas and remains in the users' body where it is further warmed, retracting extra energy from the body.

Preferably, the temperature of the breathing gas and the particles is about $-3°$ C. when entering the nose of the breathing creature, such that at least a substantial part of the particles melts before the breathing gas is exhaled again. For example, a sensor 132 may be provided near the gas outlet to monitor the diameter of the particles in the breathing gas and/or the temperature of the breathing gas, which information can be used to adjust the gas conditioning means. To prevent the breathing gas and the particles from warming up in the flexible duct 13 of the gas supply means, the duct can for example be isolated and/or provided with cooling means.

A device according to the invention thus provides a breathing gas which is conditioned by reducing its temperature, to increase the metabolism of a breathing creature breathing the gas. Because of this additional use of energy, the weight loss of the user increases. With a device according to the invention the weight loss of the user may be managed such that the weight loss is increased.

The exemplary device shown may be used by a breathing creature to breathe air from the surroundings while the gas conditioning means condition said air. The gas conditioning means are configured to condition the breathing gas such that the temperature of the breathing gas is lower than the surrounding temperature, which is in normal circumstances between $5°$ C. on a cool day outside to $25°$ C. on a warm day or inside. Preferably, the gas conditioning means are configured to condition the breathing gas such that the temperature of the breathing gas is between $-30$ and $-1°$ C. lower than the surrounding temperature. Thus, the temperature of the conditioned breathing gas is lower than the temperature of surroundings. Breathing the conditioned breathing gas takes more energy from the user's body than breathing the air of the surroundings, because the relatively cool conditioned breathing gas takes more energy warming up while inside the body of the user.

In the embodiment shown the breathing gas is cooled by a cooling duct running within the breathing gas transport duct, thus cooling the gas and small droplets added to the breathing gas. In an alternative, the gas conditioning means may be configured to subject the breathing gas and the added particles or droplets to frost, or to an alternative phase change material for a cooling medium.

In the embodiment shown, droplets of water are added to the breathing gas. Alternatively, the gas conditioning means may be configured to add a fluid, such as water, in the form of a vapour or gas, or in the form of frozen particles. The gas conditioning means may for example also be configured to generate particles of ice and to add these particles to the breathing gas. For example, the device may comprise cooling elements to freeze water into bodies of ice, or the device may comprise a space for storing bodies of ice formed outside the device, for example in a separate fridge. The device may further comprise automatic means for crunching the bodies of ice into small particles or for example a rasp for grating the body of ice to generate small particles, which particles are then added to the flow of breathing gas.

In a preferred embodiment the gas conditioning means comprise at least one cooling element for forming a body of ice thereupon, preferably by way of guiding moist air along its cooled surface. The cooling element is movably supported relative to a scraper body for moving the body of ice along the scraper body to generate small ice particles. In a further alternative the rasp or grater is also formed by a body of ice.

By guiding the breathing gas along the ice being crunched or gartered, the particles of ice may be introduced onto the stream of breathing gas.

In an alternative embodiment, a device according to the invention comprises gas conditioning means configured to expand a pressurised breathing gas to lower the temperature of the breathing gas. Preferably, the gas conditioning means are furthermore conditioned to add a fluid in the form of vapour or gas to the breathing gas prior to expanding, for forming particles comprising frozen fluid within said breathing gas upon expansion of the breathing gas. The vapour or gas may also be added during the expansion of the breathing gas.

In a further preferred embodiment the breathing device and in particular the gas conditioning means are configured to add an additive to the breathing gas. For example, cartridges comprising an additive in gaseous or liquid form may be provided for inserting in a cradle in the gas conditioning means for adding the additive to the breathing gas. Control means may be provided for controlling the amount of additive added, the moment at which it is added, for example at the end of a time interval, etc.

For example, the gas conditioning means may be configured to add oxygen to the breathing gas, thus providing a user with extra energy during exercising. Also, an aromatic substance may be added to the breathing gas. For example by adding menthol aroma the gas user may experience a sense of freshness which motivates him during excercising. For example by adding lavender aroma the breathing gas may relax the user which may be beneficial when the device is used during sleep. Furthermore, a medicine may be added to the breathing gas, for example insulin for use by diabetics or bronchodilators for the treatment of asthma.

A device according to the invention may also be provided with means for treating air, such as a filter for removing pollutants such as dust particles from the air to be used as a breathing gas to provide the breathing creature with clean air.

The embodiment shown uses the air out of the surrounding environment for conditioning. In an alternative embodiment, the breathing gas may for example also be provided from a pressurised reservoir. Such a reservoir may for example be a refillable reservoir comprised within the device or for example be a separate canister connectable to the air inlet of the device. For example, when the air in the environment is relatively warm it may be profitable to provide the gas conditioning means with a breathing gas which is cooler than the air of the environment, thus limiting the work of the conditioning means to be done to condition the breathing gas by cooling. By providing the device with a pressurised breathing gas the gas conditioning means may be limited in size and energy consumption. Thus the device can be small and easy to handle.

Furthermore, when the breathing gas is provided under pressure, it may not be necessary to use a fan, or similar means such as a bellow, to drive the breathing gas via the transport ducts. The supply of flow of gas may be simply be regulated via an adjustable valve.

The gas conditioning means, in particular the gas inlet may for example also be connectable to a gas pre-conditioning means, for conditioning the breathing gas, such as the air from the surroundings, prior to entering the device. Thus the gas conditioning means of the device only have to cool the air a little or not at all. By providing the device with a pre conditioned breathing gas the gas conditioning means may be limited in size and energy consumption. Thus the device can be small and easy to handle which may enhance its fitness to for example be worn on the body while the user is exercising.

Furthermore, the device may be provided with gas supply means which can be disconnected from the conditioning means for enabling use of the device with different gas supply means. Thus a user can replace the gas supply means, or part thereof such as the gas outlet or mask. For example in a gym or fitness centre or medical centre, gas conditioning means may be provided which are mounted to sports equipment (fitness apparatus 20) such as an exercise machine or ergo meter, for example a stationary bicycle, treadmill or rowing machine. A user of the exercise machine can use his personal gas supply means to provide himself with conditioned breathing gas from the fixed gas conditioning means. Because each user can connect his gas supply means to the device, multiple users can subsequently use the device, without the need of the gas outlet to be cleaned.

In a further preferred embodiment, the device is provided with means for connecting multiple gas supply means to the gas conditioning means, thus enabling multiple users to use the same device at the same time. In a preferred embodiment the device comprises detection means for detecting how many users are connected and to adjust the provision of conditioned breathing gas in relation to the number of detected users.

A device according to the invention may be designed as a portable device for example for use during walking or cycling, or as a more robust design for example for use while sleeping, doing a work out on a home trainer, etc. A device can for example be worn via a belt, in a back pack, etc.

Furthermore, a device according to the invention may also be used in combination with a gas duct comprising a mouthpiece, or a gas duct comprising a combination of a nosepiece and a mouthpiece. The positioning means connected to the air duct configured to fix the actual gas outlets in the nose openings of a user may be provided with extra securing means for securing it near or in the nose of the user and or his mouth, such that the mouthpiece may be used while sleeping.

In an embodiment according the invention the device comprises control means for controlling the gas conditioning means, in particular the cooling means and the humidifying means. The device may further comprise control means for controlling the gas supply means, for example by way of a valve or fan to control the gas flow.

Preferably a user, or for example a fitness instructor, can control the process parameters such as the speed of the flow of breathing gas, the amount and size of particles added to the breathing gas, the amount of additive added to the breathing gas and/or the temperature of the breathing gas. A user may for example switch off the adding of particles to inhale cooled breathing gas only.

In addition the control means may be provided with a control system and sensors for partially or fully automated control of the gas conditioning means. For example a temperature sensor 134 may be provided near the gas outlet to detect the temperature of the conditioned breathing gas. The detected temperature can be provided to the control system and/or display to enable adjustment of the gas conditioning means, in particular the cooling means, by the control system or a user of the device. Similarly, a sensor 132 may be provided to monitor the diameter of the particles in the breathing gas, for example near the gas outlet, which information can be used to adjust the gas conditioning means.

In a further preferred embodiment, a control system controls the parameters relative to each other such that the user may enter for example only one parameter or a user profile such as "low intensity" for use of the device while sleeping or "high intensity" for use of the device during exercising.

A device according to the invention may be provided with an active or a passive system, or both. With an active system the flow of breathing gas is synchronized with the breathing pattern of the breathing creature using the device. A control system detects the breathing pattern of the breathing creature and on basis of that information regulates the speed and pressure of the flow of breathing gas to match the breathing pattern. An active system is especially suitable for providing a breathing gas to a sleeping user.

With a passive system the breathing gas is provided at a constant speed and pressure, which makes it easier to manage the flow and cooling of the breathing gas by a control system.

A device according to the invention may be provided with a power source such as a battery for running the conditioning means and/or the control means etc. In addition, or as an alternative, the device may be adapted to be connected to the electricity grid.

The invention furthermore provides a method for managing the weight of a breathing creature, for example a human being. The method comprises conditioning a breathing gas and supplying the breathing gas to the nose of the creature with a device as disclosed. The breathing gas may be conditioned by adding particles comprising frozen fluid to the breathing gas. Furthermore, the temperature of the breathing gas may be lowered to form particles comprising frozen fluid within the breathing gas.

Thus, a device according to the invention can be used in a method for conditioning a breathing gas by lowering the temperature of the breathing gas to increase the metabolism of a breathing creature, such as a human being, breathing the conditioned breathing gas to manage the weight, and in particular to induce weight reduction, of the human being.

Preferably, a substance is added to the breathing gas in liquid or gaseous form to form the particles in the breathing gas. The substance may also be added in the form of solid i.e. frozen particles. Preferably the temperature of the breathing gas is lowered, for example by use of a compressor and expansion valve, to form particles comprising frozen fluid within the breathing gas. Alternatively, particles comprising frozen fluid may be added to the breathing gas. Preferably, the frozen particles are ice crystals created from water droplets of water vapour.

In a further embodiment according to the invention, the device may be adjustable to provide only a cooled breathing gas to the users' nose, the gas not comprising frozen fluid particles, to limit the intake of liquid by the user of the device.

According to a further aspect of the invention the invention provides a further device for providing a breathing gas. Said device comprises gas supply means for supplying a breathing gas to a user's nose and gas conditioning means for conditioning the breathing gas. The gas conditioning means may be connected to the gas supply means and condition the breathing gas before said breathing gas reaches the nose of the user. The device is used for controlling the weight loss of the user.

The gas supply means may comprise at least one gas outlet which is configured to in use be located near and/or in an opening of the users nose. The gas supply means may comprise positioning means for positioning the at least one gas outlet near and/or in the opening of the users nose. The gas supply means may comprise positioning means for positioning the at least one gas outlet adjacent and/or in to the opening of the users nose.

The breathing gas may be air. The gas supply means may be configured to supply air to the user's nose and the gas conditioning means may be configured to condition the air. The gas supply means may comprise an air inlet for letting in air.

The gas conditioning means may be configured to condition the temperature of the breathing gas. The gas conditioning means may be configured to condition the temperature of the breathing gas such that the temperature of the breathing gas is between $-30$ and $60°$ C. and preferably $-15$ and $45°$ C.

An embodiment of the device according the invention comprises one or any combination of two or more of the following features; the gas conditioning means may be configured to humidify the breathing gas, the gas conditioning means may be configured to increase the level of humidity of the breathing gas, the gas conditioning means may be configured to add vapour to the breathing gas, the gas conditioning means may be configured to add an additional substance having a vapour form to the breathing gas, the gas conditioning means are configured to add vapour particles to the breathing gas, the gas conditioning means are configured to add steam to the breathing gas and the gas conditioning means are configured to moisten the breathing gas. These features facilitate the conditioning of the breathing gas.

In an embodiment of the device according to the invention, the gas conditioning means are configured to lower the temperature of the breathing gas. In this embodiment the weight loss of the user is controlled such that the weight loss is increased. Because of the low temperature of the breathing gas, the user will, due to the natural reaction of the body, use energy to make the breathing gas warmer. Because of this additional use of energy, the weight loss of the user increases. The gas conditioning means may be configured to cool the breathing gas. The gas conditioning means may be configured to condition the breathing gas such that the temperature of the breathing gas is between $-30$ and $-1°$ C. and preferably between $-15$ and $-1°$ C. The gas conditioning means may be configured to condition the breathing gas such that the temperature of the breathing gas is lower than the surrounding temperature. The gas conditioning means may be configured to condition the breathing gas such that the temperature of the breathing gas is between $-30$ and $-1°$ C. and preferably between $-15$ and $-1°$ C. lower than the surrounding temperature. The gas conditioning means may be configured to subject the breathing gas to frost. The gas conditioning means may be configured to form particles comprising ice in the breathing gas. The gas conditioning means may be configured to form ice particles in the breathing gas. The gas conditioning means may be configured to form ice crystals in the breathing air. The gas conditioning means may be configured to subject the vapour to frost. The gas conditioning means may be configured to subject the vapour particles to frost. The gas conditioning means may be configured to subject the steam to frost. The gas conditioning means may be configured to lower the temperature such that vapour particles present in the breathing gas freeze and form ice particles.

In an embodiment of the device according the invention, the gas conditioning means are configured to increase the temperature of the breathing gas. In this embodiment the weight loss of the user is controlled such that the weight loss is reduced. Because of the high temperature of the breathing gas, the user will, due to the natural reaction of the body, use less energy because the breathing gas (almost) does not need to be made warmer by the user. Because of this reduction in use of energy, the weight loss of the user reduces.

In an embodiment of the device according the invention, the gas conditioning means may be configured to add an additive to the breathing gas. The gas conditioning means may be configured to add oxygen to the breathing gas. The gas conditioning means may be configured to add an aromatic substance to the breathing gas. The gas conditioning means are configured to add a medicine to the breathing gas.

In an embodiment according the invention the device comprises control means for controlling the gas conditioning means. The device may comprise further control means for controlling the gas supply means. The gas supply means may comprise drive means for transporting the breathing gas. The gas supply means may comprise a gas duct. The gas conditioning means may comprise humidifying means for increasing the level of humidity of the breathing gas. The gas conditioning means may comprise cooling means for cooling the breathing gas. The gas conditioning means may comprise warming means for warming the breathing gas.

The device according to the invention may be used for breathing air from the surroundings, while the gas conditioning means conditions said air. The gas conditioning means may condition said air such that the temperature of said air is lower than the temperature of the surroundings. The conditioning means may condition said air such that the temperature of said air is higher than the temperature of the surroundings.

The invention further relates to the use of a device according the invention. The invention also relates to a method for controlling the weight loss of a breathing creature, for example a human, by supplying a conditioned breathing gas to the nose of the creature with a device according to the invention. The breathing gas may be conditioned such that the temperature of the breathing gas is lowered and/or increased.

Figure 2:
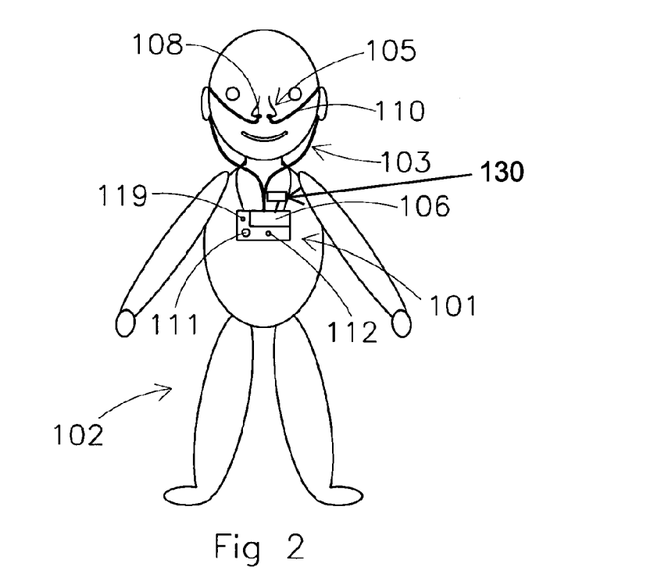
FIG. 2 schematically shows a user using an embodiment of an alternative device according the invention.
Figure 3:
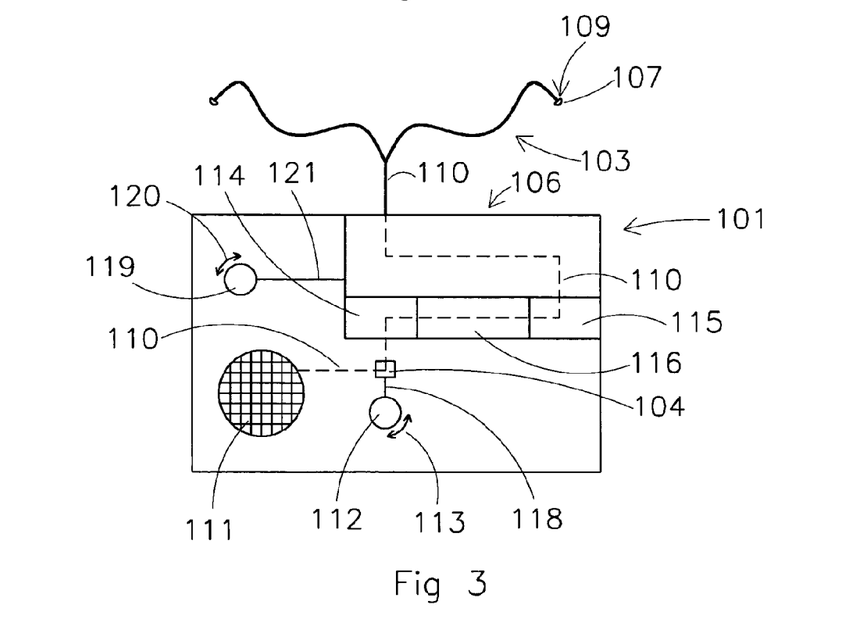
FIG. 3 is a schematic view partially in section of the alternative device of FIG. 2.

The invention is in the enclosed figures explained in more detail, wherein FIG. 2 shows a user using an embodiment of the device according the invention and FIG. 3 shows the device of FIG. 2 in an enlarged view.

FIG. 2 shows a user 102 using an embodiment of the device 101 according the invention. The user is a breathing creature, more specifically a human. The device 101 comprises gas supply means 103 for supplying a breathing gas to the nose 105 of the user 102. The gas supply means 103 comprise positioning means (109 of FIG. 3) to position the gas outlets (107 of FIG. 3) in the openings 108 of the nose 105. In use, the user 102 breaths the breathing gas in via his nose 102. The device 101 comprises gas conditioning means 106 for conditioning the breathing gas. A sensor 130 is provided for placement on the skin of the person using the device, and wherein the control system controls the gas conditioning means on the basis of the registered body temperature of the person to control the energy used by the person in warming the breathing gas.

The device 101 uses air as breathing gas. The gas supply means 103 comprise an air inlet 111 for letting in air from the surroundings. The gas conditioning means 106 are configured to condition said air. The gas conditioning means 106 are configured to lower the temperature of the air and/or to condition the level of humidity of the air.

The device 101 is in FIG. 3 shown in an enlarged view. Some elements located inside the device 101 are shown for clarity reasons. The device 101 comprises an air inlet 111 and two gas outlets 107. A gas duct 110 extends between said inlet 111 and outlets 107. The gas duct 110 connects the air inlet 111 with drive means 104 which are configured to suck air via the air inlet 111 in the air duct 110. Control means 112 are via a communication line 118 connected to the drive means 104. The air supply of the gas supply means 103 is adjustable via said control means 112. The drive means 104 are controllable by rotating the control means 112 in the direction shown by arrow 113. The gas duct 110 extends further from the drive means 104 and through humidifying means 114. The drive means 104 are configured to blow the air through said part of the air duct 110. The humidifying means 114 are configured to increase the level of humidity in the air by adding steam to the air. The gas duct 110 extends further from the humidifying means 114 through cooling means 115. The cooling means 115 are configured to cool the air. The gas conditioning means 106 are with a second communication line 121 connected to second control means 119. The gas conditioning means 106 are controllable by rotating the second control means 119 in the direction of arrow 120. The degree in which the air is conditioned is adjustable by the second control means 119. The gas conditioning means 106 are controllable such that the humidifying means 114, the cooling means 115 may be used separately or in combination with each other. This means that in use the humidifying means 114 and/or the cooling means 115 may be used. The gas duct 110 extends from the gas conditioning means 106 to the outlets 107. Positioning means 109 are connected to the air duct 110 adjacent to the outlets 107. The positioning means 109 are configured to fix the outlets 107 in the nose openings of a user.

This means that the device 101 may be used for breathing air from the surroundings, while the gas conditioning means 106 conditions said air. The gas conditioning means 106 may condition said air such that the temperature of said air is lower than the temperature of the surroundings. The conditioning means 106 may condition said air such that the temperature of said air is higher than the temperature of the surroundings.

The invention also relates to a device 101 comprising one or any combination of two or more of the following features: gas supply means 103, drive means 104, gas conditioning means 106, gas outlet 107, opening nose 108, positioning means 109, gas duct 110, air inlet 111, first control means 112, humidifying means 114, cooling means 115, warming means 116, communication line 118, second control means 119, second communication line 121.

It is noted that under mammals, humans as well as other mammalians are understood herein, such as for example pets like dogs or cats, as also other mammalians such as horses or cattle. The method is suitably used in humans, preferably in moderate overweight humans (BMI 25-30), more preferably in obese people (adipose, BMI>30).

From the foregoing, it will be clear to the skilled person, that within the framework of invention as set forth in the claims also many variations other than the examples described above are conceivable.

For example the gas conditioning means may in addition be configured to increase the temperature of the breathing gas, for example, such that the temperature of the breathing gas is higher than the surrounding temperature. The gas conditioning means may be configured to condition the breathing gas such that the temperature of the breathing gas is between 16 and 40° C. and preferably between 16 and 25° C. higher than the surrounding temperature, preferably such that the temperature of the breathing gas is between 36 and 60° C. and preferably between 36 and 45° C.

In such an embodiment the weight loss of the user may be controlled such that the weight loss is reduced. Because of the high temperature of the breathing gas, the user will, due to the natural reaction of the body, use less energy because the breathing gas (almost) does not need to be made warmer by the user. Because of this reduction in use of energy, the weight loss of the user reduces. Thus the weight loss of a breathing creature can be managed in a controlled manner.

For example, the gas duct may extend through warming means configured to warm the air. The degree in which the air is conditioned preferably is adjustable by the control means. The gas conditioning means may be controllable such that the humidifying means, the cooling means and the warming means may be used separately or in combination with each other. This means that in use the humidifying means and/or the cooling means and/or the warming means may be used.

Thus the breathing gas can be conditioned in a controlled manner when the device collects relatively cold air from its surroundings, for example when the user is exercising at sub zero temperatures, it can warm the air to limit de energy that will be spend by the body of the breathing creature to warm the conditioned air. This may be beneficial when the user only wants to loose a limited amount of weight, or wants to maintain a specific body weight. Also, such a device may be used to provide fluid to the nose and lungs of the breathing creature to humidify the mucous membrane, without stimulating the metabolism of the creature.

Furthermore, a device according to the invention may be provided with detection means to detect the body temperature of the breathing creature using the device. For example, the temperature may be detected via a detector 130 placed on the skin of the breathing creature, or may be derived from monitoring the temperature difference between breathing gas inhaled and breathing gas exhaled by the breathing creature. A control system may control the gas conditioning means on the basis of the registered body temperature of the breathing creature to control the energy used by the breathing creature in warming the breathing gas.

The invention claimed is:

1. An apparatus designed for providing an active person with a breathing gas for increasing the metabolism of that person, which breathing apparatus is configured as a portable device to be worn on the body of the person, via a belt or in a back pack, during exercise to provide the person with a conditioned breathing gas while exercising, the apparatus comprising:
   gas supply means for supplying the breathing gas to the person's nose, the gas supply means comprising a gas duct with a gas outlet configured to in use be located near and/or in the opening of the person's nose such that the breathing gas is adapted to enter the body of the person via the nose ducts when the person inhales;
   gas conditioning means for conditioning the breathing gas such that the temperature of the breathing gas is between −30 and −1 Degrees C, and wherein the gas conditioning means comprise a gas transport duct provided with multiple cooling ducts, which spiral within the gas transport duct to cool the gas to a temperature below the freezing point of water, and multiple water injectors, such that water droplets and/or particles are added to the breathing gas in intermediate steps and the breathing gas is subsequently subjected to stages of cooling the flow of breathing gas and droplets and/or particles, and to stages of adding more droplets to the flow of breathing gas to form particles comprising a frozen fluid in the breathing gas,
   a control device to enable the person to manually control process parameters of the apparatus.

2. The apparatus according to claim 1, further comprising a control system and a sensor for partially or fully automated control of the gas conditioning means.

3. The apparatus according to claim 2, wherein the sensor is provided for placement on the skin of the person using the device, and wherein the control system controls the gas conditioning means on the basis of a registered body temperature of the person to control energy consumption by the person for warming the breathing gas.

4. The apparatus according claim 2, the gas supply means comprising the gas outlet for providing the person with the breathing gas, and wherein the sensor is provided near the gas outlet to monitor the diameter of the particles in the breathing gas and/or the temperature of the breathing gas, which information is used to adjust the gas conditioning means such that at least a substantial part of the particles melts before the breathing gas is exhaled again.

5. The apparatus according to claim 2, wherein information provided by the sensor is used to adjust the gas conditioning means such that the temperature of the breathing gas and the particles is about −30 C when entering the nose of the person such that at least a substantial part of the particles melts before the breathing gas is exhaled again.

6. The apparatus according to claim 1, wherein the temperature of the conditioned breathing gas and/or the size of the particles is such that the particles are adapted to melt within the breathing ducts of the person, in particular in the back of the nose or throat, such that the remaining liquid can be swallowed by the person.

7. The apparatus according to claim 1, further comprising an active system comprising a control system for detecting a breathing pattern of the person using the apparatus, and for regulating the speed and pressure of the flow of breathing gas such that the flow of breathing gas is synchronized with the breathing pattern of the breathing person using the apparatus.

8. The apparatus according to claim 1, wherein the gas supply means can be disconnected from the conditioning means for enabling use of the device with different gas supply means.

9. The apparatus according to claim 1, comprising multiple gas supply means for enabling multiple people to use the same gas conditioning means at the same time.

10. The apparatus according to claim 1, wherein the gas conditioning means are configured to add a fluid in the form of droplets, a vapour or gas, or frozen particles, to the breathing gas.

11. The apparatus according to claim 1, wherein the frozen fluid is ice particles.

12. The apparatus according to claim 1, wherein the temperature of the breathing gas is between −15 and −1° C.

13. The apparatus according to claim 1, wherein the process parameters include the speed of the flow of breathing gas, the amount and size of particles added to the breathing gas, the amount of an additive added to the breathing gas and/or the temperature of the breathing gas.

14. A fitness system comprising:
   a fitness apparatus, comprising one of an ergo meter, stationary bicycle, treadmill or rowing machine; and
   a breathing apparatus is connected to the fitness apparatus and is designed for providing an active person with a breathing gas for increasing the metabolism of that person, the breathing apparatus comprising: gas supply means for supplying the breathing gas to the person's nose, the gas supply means comprising a gas duct with a gas outlet configured to in use be located near and/or in the opening of the person's nose such that the breathing gas is adapted to enter the body of the person via the nose ducts when the person inhales; and
   gas conditioning means for conditioning the breathing gas, wherein the gas conditioning means are configured to add droplets to the breathing gas in intermediate steps, and wherein the gas conditioning means comprise a gas transport duct provided with multiple cooling ducts, which spiral within the gas transport duct to cool the gas to a temperature below the freezing point of water, and multiple water injectors, such that water droplets and/or particles are added to the breathing gas in intermediate steps and the breathing gas is subsequently subjected to stages of cooling the flow of breathing gas and droplets and/or particles, and to stages of adding more droplets to the flow of breathing gas to form particles comprising a frozen fluid in the breathing gas, for providing the person using the fitness apparatus to exercise with the conditioned breathing gas,
   a control device to enable the person to control process parameters of the breathing apparatus.

* * * * *